United States Patent [19]
Sutter et al.

[11] Patent Number: 5,533,539
[45] Date of Patent: Jul. 9, 1996

[54] APPARATUS FOR INTENSIVE CLEANING OF MEDICAL ARTICLES

[75] Inventors: Ralf Sutter, Weinheim; Lutz Beerstecher, Bensheim; David Hruza, Bad Waldsee; Raimund Stetter-Alle, Ulm; Karl Trackl, Langenau, all of Germany

[73] Assignee: Siemens Aktiengesellschaft, Munich, Germany

[21] Appl. No.: 274,325

[22] Filed: Jul. 13, 1994

[30] Foreign Application Priority Data

Jul. 15, 1993 [DE] Germany ............... 43 23 816.5
Apr. 26, 1994 [EP] European Pat. Off. ........... 94106516

[51] Int. Cl.⁶ ........................................ B08B 3/02
[52] U.S. Cl. ............. 134/95.2; 134/95.3; 134/102.2; 134/102.3; 134/170; 134/171; 422/28; 422/300
[58] Field of Search .................... 134/95.2, 95.3, 134/102.1, 102.2, 102.3, 98.1, 169 R, 170, 171, 22.12; 422/28, 32, 33, 300

[56] References Cited

U.S. PATENT DOCUMENTS

| | | | |
|---|---|---|---|
| 2,818,076 | 12/1957 | Erling | 134/102.1 |
| 2,827,063 | 3/1958 | Roy | 134/171 |
| 3,102,666 | 9/1963 | Fresard | 222/373 |
| 4,015,614 | 4/1977 | Jonsson et al. | 134/170 X |
| 4,892,112 | 1/1990 | Knetsch | 134/102.1 |
| 5,007,444 | 4/1991 | Sundholm | 134/102.1 |
| 5,057,283 | 10/1991 | Guggenheim et al. | 422/116 |
| 5,137,689 | 8/1992 | Cantrell | 422/28 |
| 5,183,513 | 2/1993 | Sajewski | 134/22.12 |
| 5,197,499 | 3/1993 | Bodenmiller et al. | 134/95.2 |
| 5,225,160 | 7/1993 | Sanford et al. | 422/28 |
| 5,266,275 | 11/1993 | Faddis | 422/33 X |
| 5,271,893 | 12/1993 | Newman | 422/26 |
| 5,308,579 | 5/1994 | Melon et al. | 422/28 |
| 5,348,711 | 9/1994 | Johnson et al. | 134/170 X |

FOREIGN PATENT DOCUMENTS

| | | |
|---|---|---|
| 0300945 | 1/1989 | European Pat. Off. . |
| 0494031 | 7/1992 | European Pat. Off. . |
| 561205 | 10/1932 | Germany . |
| 1185348 | 1/1965 | Germany . |
| 1403669 | 10/1968 | Germany . |
| 3018872 | 11/1981 | Germany . |
| 3117264 | 11/1982 | Germany . |
| 3916446 | 3/1990 | Germany . |
| 4130233 | 9/1992 | Germany . |
| 4211744 | 4/1993 | Germany . |

*Primary Examiner*—Philip R. Coe
*Attorney, Agent, or Firm*—Hill, Steadman & Simpson

[57] ABSTRACT

A method for cleaning medical instruments, particularly dental articles and dental instruments, with a cleaning fluid applied in a pulsating fashion comprises a step of gas being supplied to the cleaning fluid under high pressure in a pulsating fashion in pulse pauses of the fluid. The apparatus comprises a cassette into which the articles are placed and the cassette is inserted into a chamber of the apparatus which is closable pressure-tight. The cassette can contain adapters for holding the articles and the apparatus includes means for supplying both pulsating cleaning fluid as well as the pulses of gas or air.

20 Claims, 8 Drawing Sheets

APPARATUS FOR INTENSIVE CLEANING OF MEDICAL ARTICLES

BACKGROUND OF THE INVENTION

The present invention is directed to a method as well as to an apparatus for the intensive cleaning of medical devices or instruments, particularly dental instruments, as well as potentially other articles falling within this area of use.

In the medical field, particularly dental field, the instruments utilized therein must be subjected to an intensive cleaning after a patient treatment. In the dental field, these instruments include spray handpieces, drilling and grinding instruments, which may be angle pieces and turbine handpieces, as well as various other hand instruments. Over and above this, other articles, such as dental bridges, dental braces, dentures or the like must be subjected to such an intensive cleaning, which is especially true in the laboratory area.

German Offenlegungsschrift 30 18 872 discloses a method for cleaning articles, particularly medical apparatus, wherein the cleaning fluid is intermittently sprayed onto the articles so that there is a pause between the spray events which are so long that the film of cleaning fluid formed on the articles has departed before another spray event occurs. The spraying of the cleaning fluid in the known method occurs with compressed air. The apparatus working according to this method is constructed in the fashion of a dishwasher, i.e., the articles are sprayed, on the one hand, from above via a pivot arm occupied with spraying nozzles and, on the other hand, from below via what is referred to as a long nozzle that extends into the interior of the articles to be cleaned.

German Offenlegungsschrift 39 16 446 discloses, for general cleaning purposes, particularly for cleaning rocks, buildings or the like, the concept of continually and/or periodically adding air in controllable fashion to a jet of pressurized water on the basis of an injector effect. To this end, a mixing chamber having various air entry openings via which air is drawn in precedes the pressurized water nozzle at the pressurized water exit.

SUMMARY OF THE INVENTION

The object of the present invention is to provide a method and apparatus that is well-suited for intensive cleaning of medical, particularly dental, articles. What is characteristic of this method of the invention is that air having a higher pressure is introduced in a pulsating fashion into the delivery line of the cleaning fluid to the nozzles in the pulse pauses of the cleaning fluid.

To accomplish these goals, the invention is directed to a method for intensively cleaning medical devices instruments or articles, including dental instruments and other articles falling in the area of dental employment, which method comprises supplying a cleaning fluid under pressure and directing the fluid onto the instruments via nozzles with the improvement being that the cleaning fluid is supplied in a pulsating fashion and air under high pressure is introduced in a pulsating fashion into the delivery line of the cleaning fluid to the nozzles in the pulse pauses of the fluid delivery.

An apparatus operating according to this method comprises a cassette that accepts the articles and that can be placed into a chamber closable pressure-tight wherein the cleaning process is carried out. The cassette contains adapters for holding the articles. A plurality of nozzles that are designationally directed onto the articles are arranged around the held articles. Cleaning fluid is conducted into the interior surface of the article by the nozzles. It has been surprisingly shown that the kinetic energy of the fluid is elevated so that when a gas is supplied to the cleaning fluid in the pulse pauses in a pulsating fashion, preferably with chronologically short pulses, such that an extremely high cleaning effect can be achieved with low water consumption even without cleaning agents. A critical effect of the cleaning is thus obtained wherein the high-energy water jet is generated with gas supplied surge-like to the water, preferably with compressed air. The pulse frequency for this surge-like delivery of the gas lies at approximately 3 Hz.

Other advantages and features of the invention will be readily apparent from the following description of the preferred embodiments, the drawings and claims.

Figure 1:
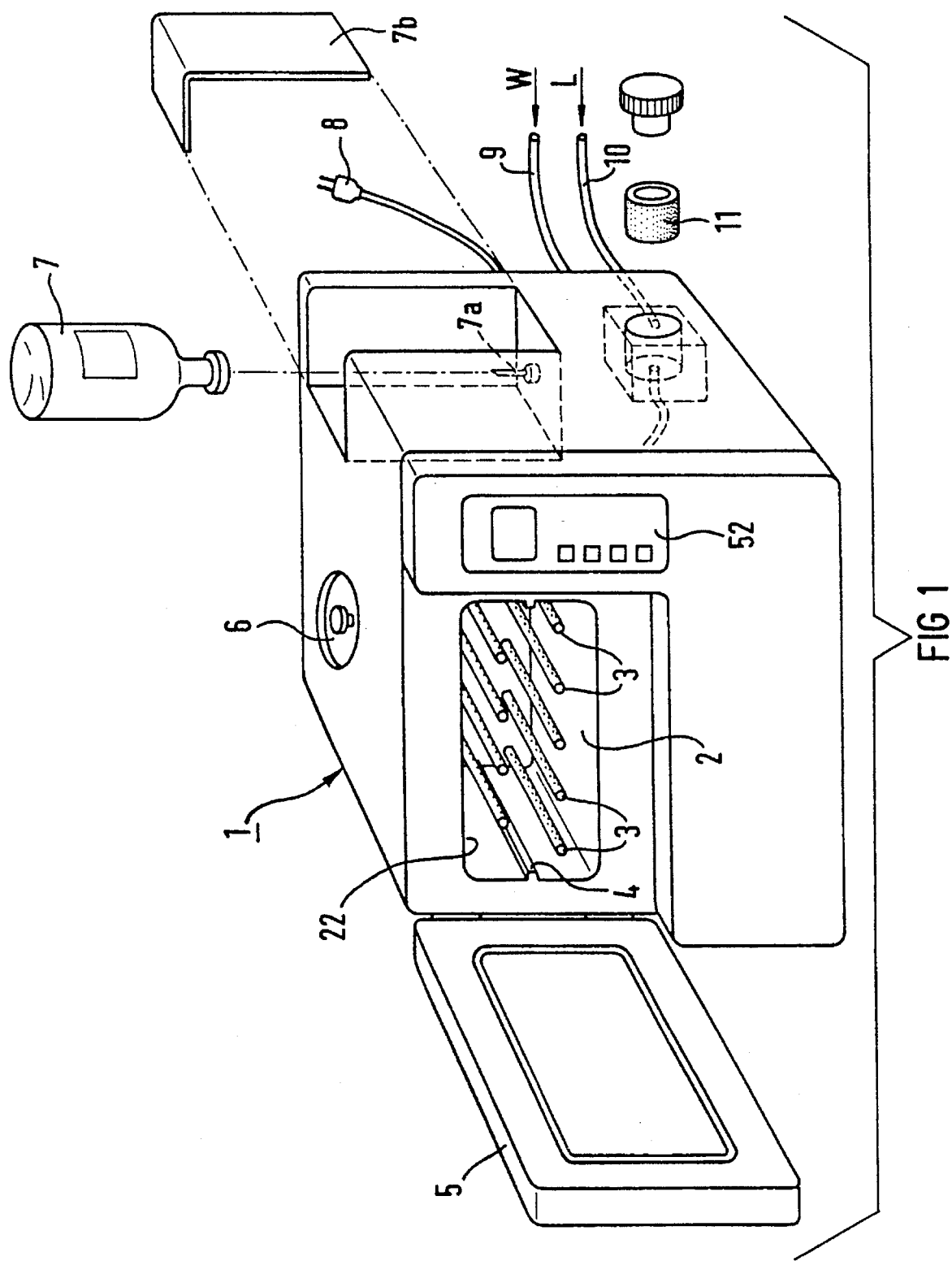
FIG. 1 is a schematic partially exploded perspective view of an embodiment of the apparatus of the present invention.
Figure 2:
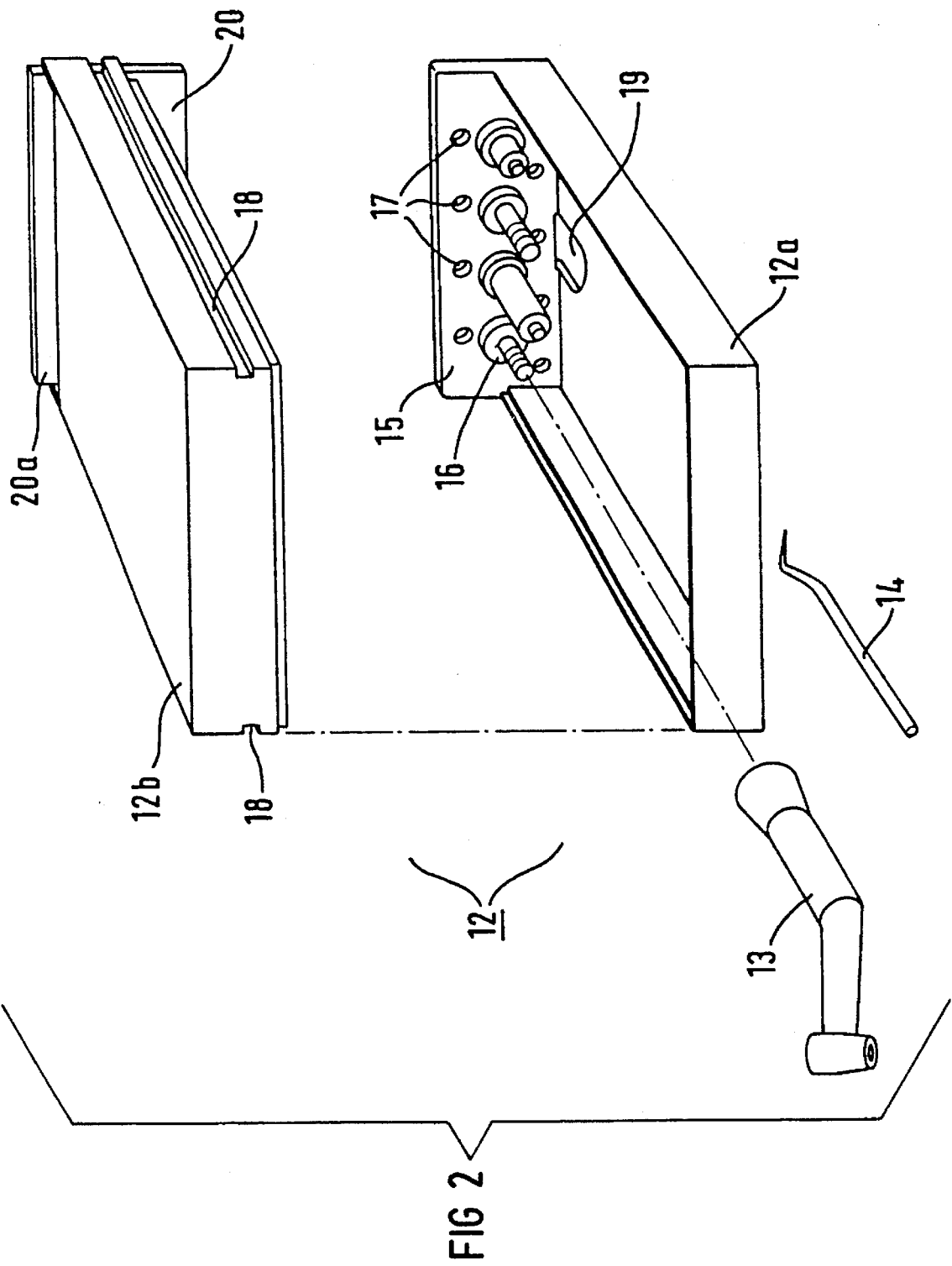
FIG. 2 is an exploded perspective view of an instrument cassette in accordance with the present invention.
Figure 6:
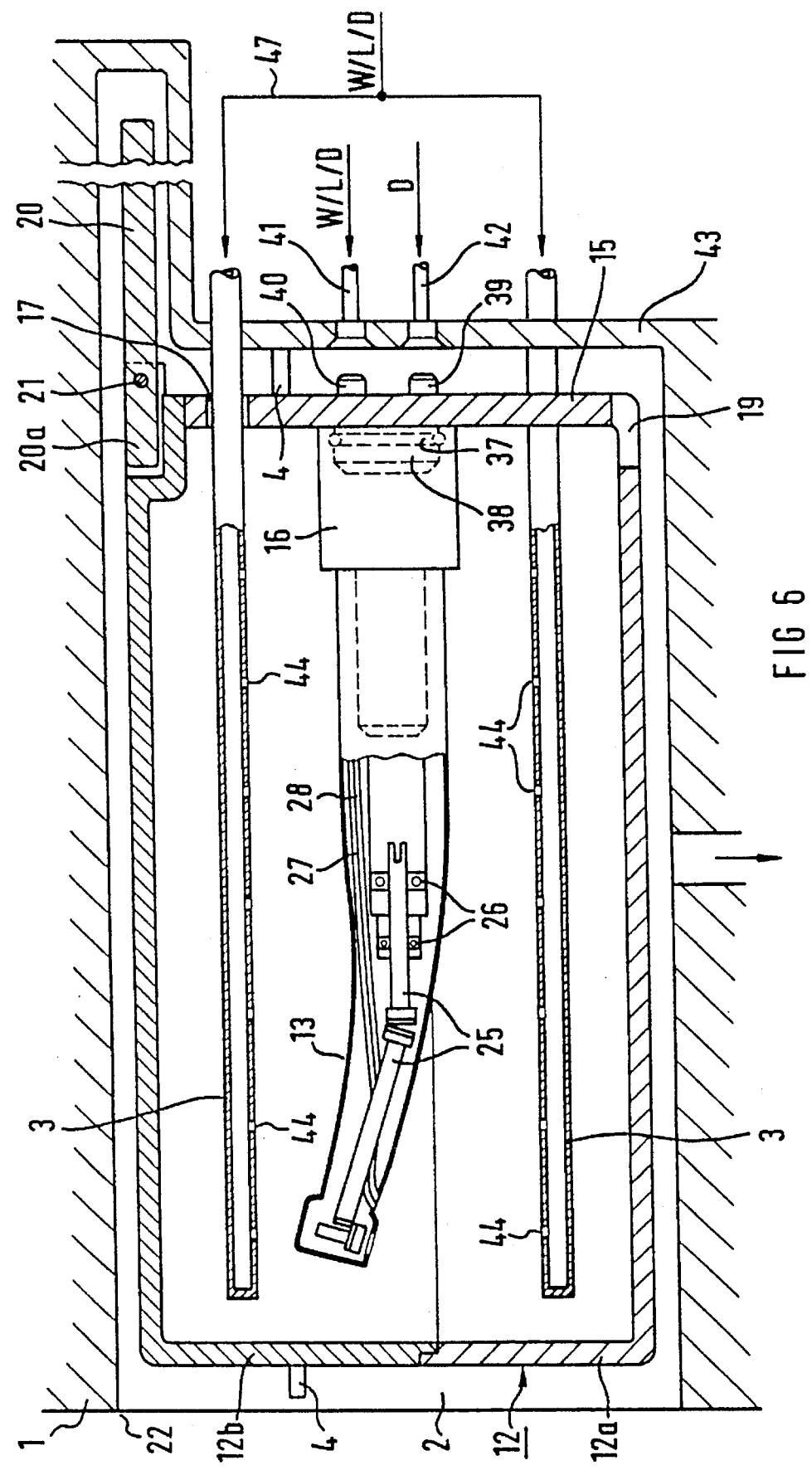
FIG. 6 is a longitudinal cross sectional view of the cassette of the present invention disposed in the apparatus with portions in elevation for purposes of illustration.

DESCRIPTION OF THE PREFERRED EMBODIMENT;

The principles of the present invention are particularly useful when incorporated in a cassette 12 illustrated in FIGS. 2 and 6, which is used with an apparatus, generally indicated at 1 in FIG. 1.

The apparatus 1 is used for the purpose of a hygienic preparation of various dental instruments. The apparatus contains a housing which forms a chamber 2 on the front side for the acceptance of a cassette 12 (see FIG. 2). The chamber 2 has a plurality of nozzle arms 3 (nine are illustrated) which project into the chamber 2. The instruments are capable of being sprayed on the outside with the assistance of these nozzle arms 3. The chamber 2 has guide beads 4 for the guidance of the cassette arranged on both sides. The chamber 2 can be closed pressure-tight on its front side with a cover or door 5, which operates in a known way.

The housing for the apparatus 1 has a container for demineralized or distilled water which is located adjacent an upper surface of the housing and has a filling opening 6. On the right-hand side near the rear of the apparatus, the apparatus 1 has a diaphragm closure provided in a known way, which closure is punctured by a connection shank 7a when the container 7 is placed on the connection shank so that removal of the lubricant can occur. A door or lid 7b can close the nitch that receives the container 7 once the container has been inserted.

The apparatus also has an electrical lead 8, a line 9 for receiving water indicated by the arrow W and an air line 10 which receives compressed air indicated by the arrow L. To assure that a largely germ-free gas or air is available for the method steps set forth in greater detail below, the air line 10 passes through a filter chamber which receives a removable and, thus, replaceable sterile filter 11.

The cassette 12, as illustrated in FIG. 2 in an exploded view, is introducible into the chamber 2 and will receive a plurality of instruments, such as a handpiece 13 and a manual instrument 14. The instrument 13 is shown as either a handpiece or an angle piece whose inside comprises various drive parts and bearings as well as media channels. The instrument 14, by contrast, is a hand instrument that comprises no moving parts and, therefore, has no media channels. The cassette 12 is composed of a base part or a lower part 12a and an upper cassette part 12b which is removable therefrom. The lower cassette part 12a is constructed trough-like and contains four different adapters for the acceptance of differently-shaped instruments on a raised backwall 15. In the exemplary embodiment, the adapter 16 is matched to receive the instrument 13 which is accepted thereon. The four adapters are provided for instruments that comprise moving internal parts and media channels, such as, for example, handpieces, angle pieces, turbine handpieces, handpieces for removing dental tartar or spring handpieces. The instruments that contain no moving internal parts and also contain no media channels, such as, for example, hand instruments 14 in the Figure, are placed on the floor or base of the lower cassette part with a suitable holder for the purpose of preparation.

The backwall 15 of the lower cassette part 12a also contains bores 17 (nine of which are illustrated), through which the nine nozzle arms or nozzle tubes 3 of the chamber 2 can pass through when the cassette 12 is introduced into the chamber. The arrangement of the nozzle arms and of the bores 17 which correspond thereto is, respectively, a triangular arrangement around the centrally-placed adapters, as illustrated in the Figure.

The upper part 12b can be placed on the lower cassette part 12a and can be latched thereto. The upper part 12b contains lateral guide channels 18 that interact with the above-mentioned guide beads 4 of the chamber and assure the exact centering and guidance of the cassette 12 when it is inserted into the chamber 2.

At a suitable location, preferably at the floor and in the immediate proximity of the backwall 15, the cassette is provided with one or more outlet openings 19 for the discharge of the supplied cleaning fluids, as well as any condensed water. This outlet opening or outlet openings are advantageously provided with a part that automatically closes when the cassette is removed from the chamber 2. These automatic closures can be spring-loaded slides or covers.

Figure 3:
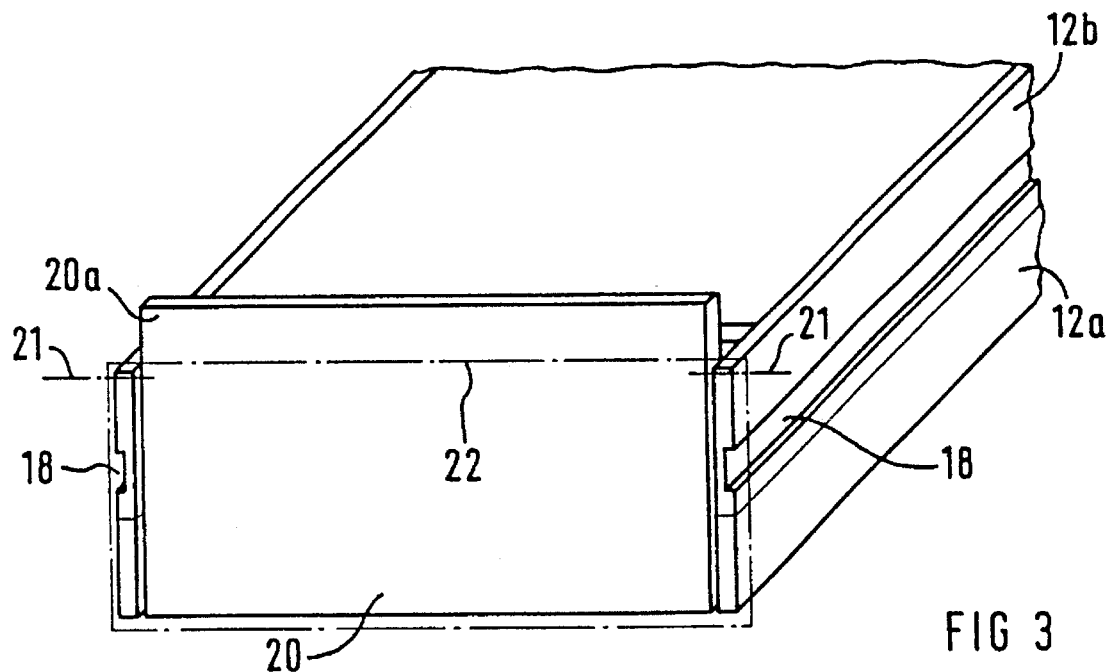
FIG. 3 is a partial perspective view taken from the rear of the cassette with a closure flap in the closed position.
Figure 4:
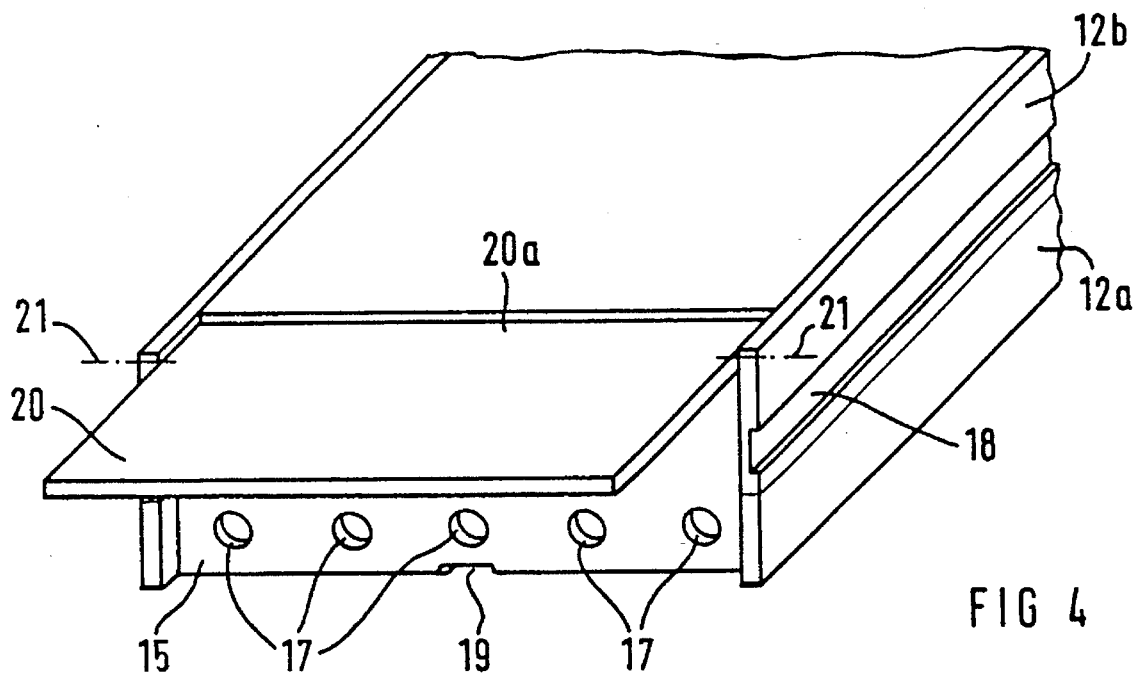
FIG. 4 is a partial perspective view similar to FIG. 3 with the closure flap in the opened position.

The upper cassette part 12b is advantageously provided with a cover on a back end, and this cover will cover, respectively, both the closing connections leading to the adapter 16 as well as the outlet openings 19 when the cassette is removed from the apparatus. As illustrated in FIGS. 3 and 4, the cover 20 is hinged around a bearing or axle 21. The movement of the cover occurs automatically when the cassette 12 is inserted into the chamber 2 of the apparatus. To accomplish this, the cover plate 20 comprises a projection 20a that strikes against the upper edge 22 (FIG. 1) of the chamber 2 upon insertion of the cassette 12 into the chamber. As a result of this, the flap will be tilted upward to the position illustrated in FIG. 4. Thus, the openings 17 located behind the cover plate, as well as the connections, which are not shown in FIG. 4, for the adapters will be uncovered or exposed. Upon removal of the cassette, the cover plate, in turn, automatically pivots or hinges down and, thus, covers the openings so that the hygienically prepared instruments located in the cassette are protected against the penetration of germs, at least for a certain time period.

Alternatively to the automatically opening and closing flap set forth above, a roller shutter element can also be provided. This will effect an automatic covering or, respectively, clearing of the openings or, respectively, connections provided in the backwall 15 with the assistance of a correspondingly provided setting means.

Figure 5:
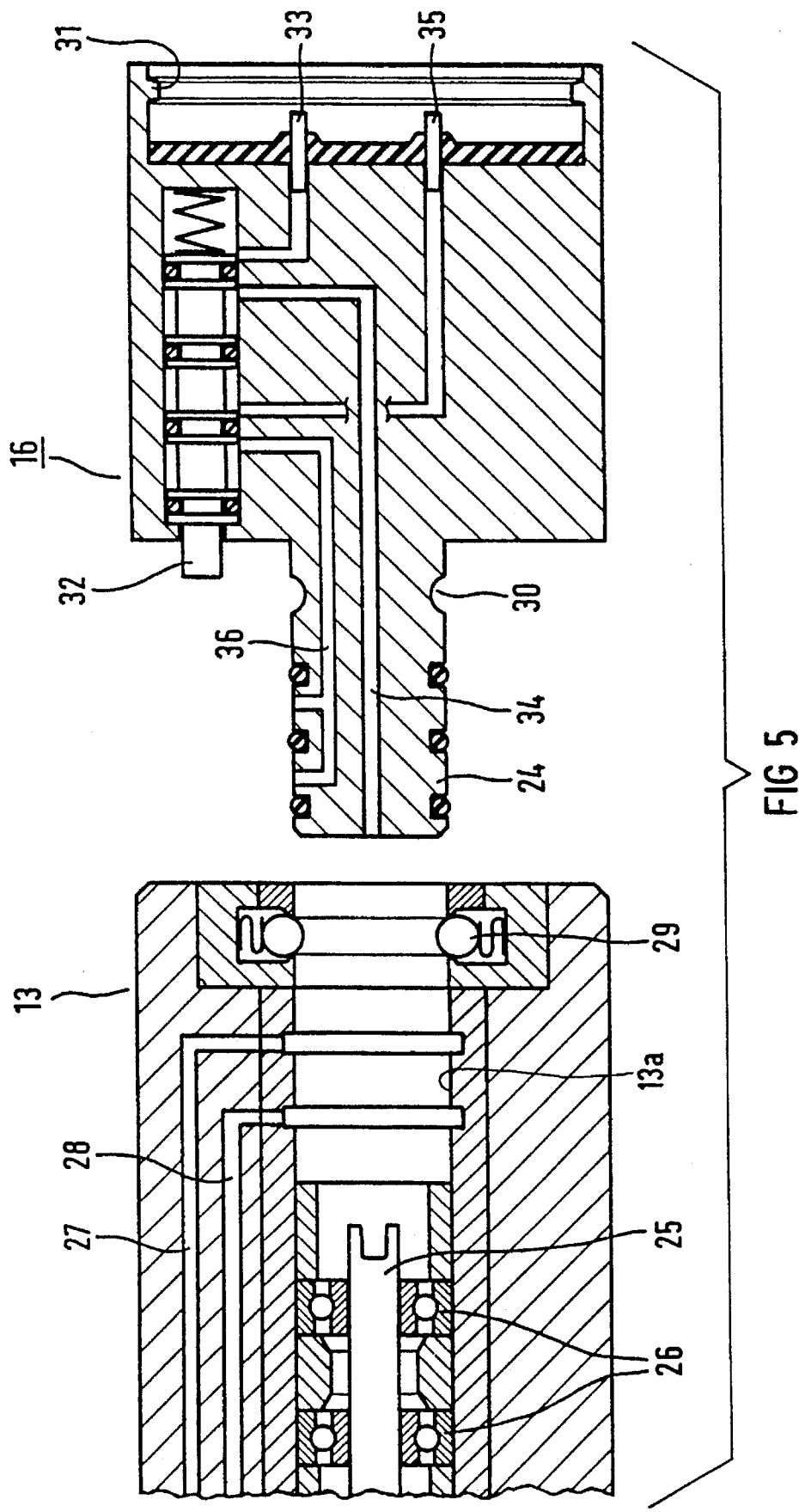
FIG. 5 is a longitudinal cross sectional view through an adapter illustrated in FIG. 2 and a portion of an instrument mating with the adapter.

The structure and function of the adapters, as well as the interaction with the instruments that can be plugged thereon, is illustrated in FIG. 5 with reference to an example of the adapter 16.

The adapter 16 is provided for connecting a hand and angle piece 13 in FIG. 2. The hand or angle piece 13, as illustrated in FIG. 5, has an axial bore 13a which receives bearing 26 that mount a drive shaft 25 for rotation. In addition, the handpiece has media channels 27, 28 for delivering cooling air and cooling water to a preparation location, and these channels proceed on the interior of the handpiece. The bore 13a adjacent an open end is provided with ball catches 29, which will be received in an annular channel, similar to 30, of a motor housing when the handpiece is inserted thereon to form a connection therewith.

The adapter 16 contains a connecting shank 24 that is structurally matched to the design of the bore 13a of the instrument. The adapter 16 is fashioned so that the end facing away from the instrument can be secured to the backwall 15 of the lower cassette part 12a in an easily detachable way. To accomplish this, it contains a catch nose 31 that interacts with an annular channel 37 of a flange or nipple 38 (FIG. 6) that is mounted on the backwall 15 of the lower cassette part 12.

The adapter 16 has a bore containing a control plunger or spool valve member 32 that is displaceable parallel to the axis of the adapter, and this plunger 32 acts against a spring force so that when the instrument 13 is plugged onto the shank 24, the control plunger 32 is depressed so that input channel 33 is connected to a centrally-placed channel 34 and an input channel 35 is connected to an aligned channel 36 which has peripheral openings that are aligned with openings for the media channels 27 and 28 of the instrument. Thus, drive air or lubricating oil can be introduced via the channel 33 to the drive shaft 25 and the bearings 26 and air and water are guided in common in the lines 27 and 28 via the channels 35 and 36.

When an instrument, such as 13, is removed from the adapter 16, the plunger valve will assume the position illustrated in FIG. 5 and interrupt the connection between the inlet channel 33 and channel 34 and also between the channel 35 and channel 36. This will prevent any supplied media or oil from being emitted from an adapter which is not occupied with an instrument.

As already mentioned, the connection dimensions with respect to the instruments are different for all four adapters mounted in the cassette in order to, thus, be able to hold different instruments. The connecting dimensions with respect to the connector 38 on the backwall 15 of the cassette, however, are the same for all adapters so that they can be easily interchanged with one another or, respectively, can be replaced by adapters having different connecting contours for different instruments.

The allocation of the individual washing and cleaning nozzles or channels is illustrated in FIG. 6 with reference to an example of the instrument 13 and adapter 16.

In a highly simplified illustration, FIG. 6 shows the arrangement of the cassette 12 in the chamber 2 in the condition wherein the cassette 12 is nearly completely introduced. Corresponding to the plurality of existing adapters, connecting flanges 38 are located on a backwall 15 of the cassette 12 and the adapter is, as already mentioned, capable of being put in place on these connecting flanges 38 in an easily detachable way. The connecting flange 38 has a coupling sleeve 40 that will form a connection with a lead 41 and a sleeve 39 forms a connection with a lead 42. The lead 42 corresponds to the lead 35 for pressurized water, compressed gas or air and steam indicated by arrow W/L/D, while the lead 42 corresponds to the channel 33 for lubricant and air indicated by arrow D.. Each of the nozzle arms 3 are arranged star-like or, respectively, triangularly around the instrument 13 and are firmly arranged in the housing wall 43 that defines the back side of the chamber 2. These tubes or arms 3 are connected to the line 47 to receive pressurized water, compressed gas and steam, as indicated by arrow W/L/D. The tubes or arms 3 are fashioned as hollow tubes and comprise a plurality of exit openings 44 that are arranged aligned at a specific angle to a surface of the instrument. The nozzle bores are advantageously arranged along the nozzle arm or tube not only in one plane but in a plurality of planes offset relative to one another by a defined angle. The offset can be advantageously arranged zig-zag or wave-like in the longitudinal direction along the reference plane.

Figure 7:
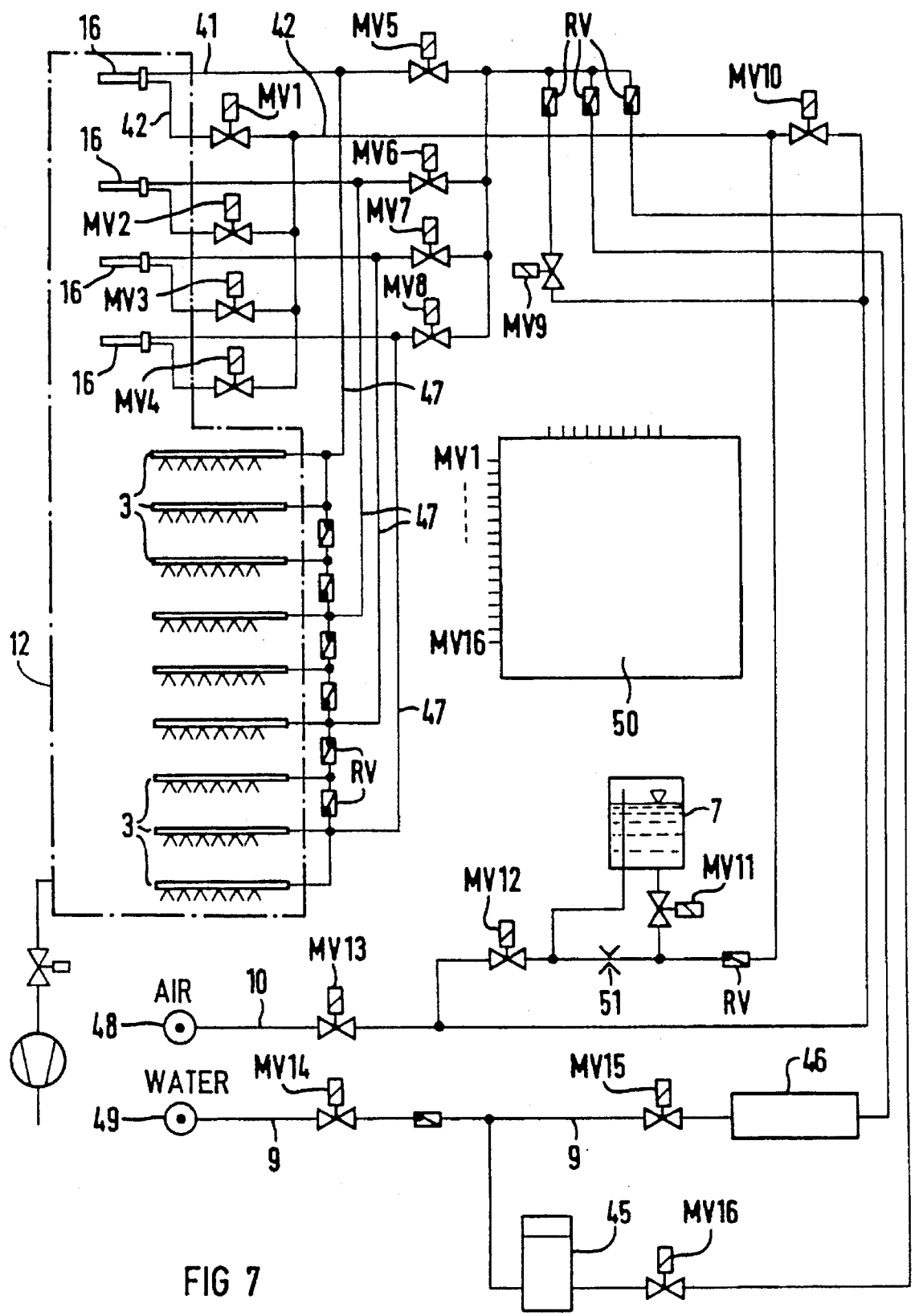
FIG. 7 is a diagram illustrating the hydraulic and pneumatic connections of the present invention.

As illustrated in FIG. 1, as well as from the following hydraulic and pneumatic connection diagram set forth in greater detail in FIG. 7, nine nozzle arms are advantageously provided for preparing a maximum of four instruments. The arrangement is therefore undertaken so that the nozzle arms are arranged in two rows and offset so that three arms are arranged around an instrument at a respective angle of 120° relative to one another.

Before the method of the invention is set forth in greater detail with reference to the drawings already described and with reference to the hydraulic and pneumatic block circuit diagram of FIG. 7, it should be pointed out that the steam generator 45 connected to the pressurized line 9, as well as the preheating means 46 for water, are accommodated in the apparatus housing in addition to the above-mentioned oil reservoir or container 7. Thus, it should be pointed out that the nozzle arms 3 length from the backwall is limited so that the lid 20 is able to tip from the closed position to the opened position as the projection 20a engages the edge 22 without striking the ends of the tubes 3.

In the hydraulic/pneumatic connection block diagram of FIG. 7, a compressed air supply source 48 and a pressurized water source 49 are connected through the lines 10 and 9, respectively. For purposes of illustration, the filters, oil separators for the compressed air as well as the overpressure valves that are standard on the input side are not illustrated for the sake of simplicity.

All solenoid valves MV1 through MV16, as well as the water heater 16 and the steam generator 45, are controlled by a microprocessor 50. Reflex or check valves RV are connected in all of the lines.

The injection of a lubricant (maintenance oil mixed with air) from the reservoir 7 occurs pneumatically here via two solenoid valves MV1 and MV12 as well as by a restriction point or throttle point 51. Alternatively, the lubricating oil could also be supplied with a suitable oil pump. The microprocessor 50 controls the valves MV1 through MV9 and MV11 through MV16 so that the agents of water, air and also lubricating oil can be supplied to the adapter 16 and to the nozzle arms 3 separately for each instrument during a method step of pre-cleaning, after-cleaning and, potentially, during the care procedure so that the instruments are cleaned and potentially maintained in chronological succession.

Figure 8:
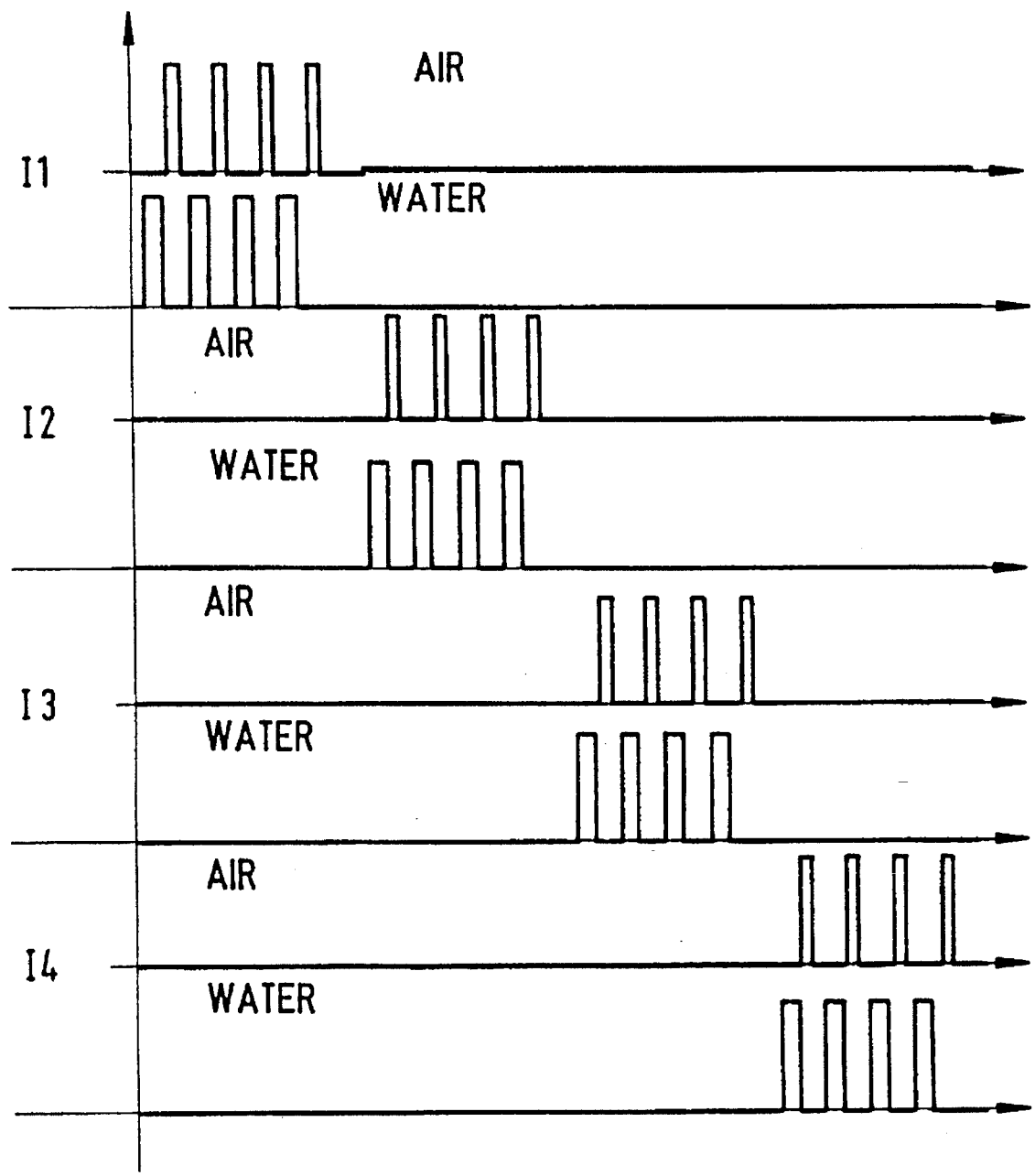
FIG. 8 is a diagram illustrating the sequence of pulses with respect to time during operation of the device of the present invention.

The chronological offset may be seen from the pulse/time diagram of FIG. 8 that shows the chronological course of the valve connections for the various agents of air and water for the four instruments referenced I1–I4. A high cleaning efficiency given a low water consumption is achieved with this chronologically successive cut-in of the agents.

The method utilizing the cassette is as follows:

The cassette 12 is charged with instruments and the instruments that have movable internal parts, such as the angle pieces, turbines, sprays or the like, are plugged onto corresponding adapters 16 of which a maximum of four are allowed in the cassette. The other instruments are placed at a holder device above the floor of the container. The cassettes are then closed by putting the upper cassette part 12b on the lower part 12a and the cassette is introduced into the chamber 2 of the apparatus. During this insertion, the rear cover 20 is lifted and, as a result thereof, the nine nozzle arms 3 extend through the bores 17 of the backwall 15 of the cassette. After the cassette has been inserted into the chamber to such an extent that the connection of lines 41 and 42 with the connectors 39 and 40 (see FIG. 6) has been produced, the cover 5 of the apparatus is closed and the apparatus is turned on.

After a self-test, which lasts approximately half a minute, a cold cleaning of the instruments occurs utilizing cold water which is supplied to the adapter 16 and to the nozzle arms 3 via leads 9 and the lines 41 and 47. The cold water is preferably supplied in a pulsating fashion whereby compressed air at high pressure, which is also pulsating, is mixed with the water into the pulse pauses illustrated in FIG. 8. A high-energy water jet is thus produced and this surprisingly causes a very thorough cleaning of the surfaces and of the inside channels as well. At the same time, the gearing channel is charged with air via a line 42 with the oil delivery valve MV11 remaining closed so that the penetration of dirt and contaminated wash water is therefore prevented. The pulse frequency with which the compressed air is supplied to the water amounts to approximately 3 Hz.

The cold cleaning is ended after about two minutes. The warm cleaning of the exterior surfaces of the instrument and of the inside channels follows thereafter, likewise with a pulsating water jet upon addition of pulsed compressed air. This procedure follows the sequence in the above-mentioned way. After about two minutes of warm cleaning, an intense after-cleaning and a vapor disinfection occurs by blowing the exterior surface of the instruments and of the media and gearing channels in the interior of the instrument off and out with the hot water or water vapor at a temperature in a range of 60° C. through 100° C. To this end, the water is heated by the heater 46 which acts as a flow-through heater. This procedure lasts for about 30–45 seconds.

Care of the moving inside parts follows this intensive after-cleaning by injecting a metered quantity of lubricant from the lubricant reservoir 7. The metering can occur dependent on the adapted instrument and amounts to about 1 gram per instrument in the injection cycle on average. This maintenance step lasts approximately half a minute.

A sterilization of the instrument then subsequently occurs, namely both from the outside as well as from the inside with saturated water steam at a temperature of approximately 134° C. given a pressure of approximately 2–2.5 bar. The sterilization procedure amounts to between 5 and 6 minutes. The sterilization procedure is followed by a drying and cooling of the instrument with cold air. The cooling procedure lasts approximately 3–5 minutes. Given an overall time of approximately 15–20 minutes for preparing the instruments, the cassette 12 with the prepared instruments can be subsequently removed and can be kept ready for use in its closed condition.

The method of execution which automatically sequences in and of itself in the described way can be varied by intervention. For example, on the basis of an appropriate program, pre-selection can be called in at a control and display panel 52 (FIG. 1) on the front side of the apparatus 1, for example, in that an intermediate drying, for example with air, is implemented following the intensive after-cleaning and disinfection of the external surfaces. An interruption can likewise occur after the maintenance in order to be able to remove articles which are not to be sterilized from the cassette.

For removing existing dry air, particularly from cavities, and particularly from cavities of the instruments, the chamber can be evacuated before the sterilization of the instruments in an advantageous modification. In order to achieve an optimum removal of the dry air, the vacuum should lie in the range of between 40 mbar and 500 mbar absolute. The vacuum can be produced according to a known fractional, multi-step method or according to a pre-vacuum method.

Extremely short times for an optimum, hygienic preparation of the instrument occur with the described method. Due to the pulsating water jet to which high-energy compressed air is supplied in surges, an especially intense cleaning of the parts is obtained. A reliable transport to the treatment location is established in that the instruments can remain in the cassette after the preparation. In addition, the cassette may be used to receive used instruments and store these used or contaminated instruments until they are to be sent for preparation. The instruments contaminated with germs after being used remain in the cassette until they are taken again therefrom and, therefore, a risk of injury to the operating personnel, among other things, is precluded as a result of this procedure. Processing, storing and transport will occur in the cassette. Since the cassette is largely closed, a sterile storing of the instrument is assured over at least an adequately long time, as measured in hours. In that the internal parts and the agent channels are flooded with hot water and steam, a relatively rapid heating time for the overall instrument occurs. A certain lime-dissolving effect is also achieved in the lines due to the fact that the lines are blown out with the water and/or steam and the exteriors are blown off with the water and/or steam. A critical advantage is that no cleaning and drive agent whatsoever need be employed.

Figure 9:
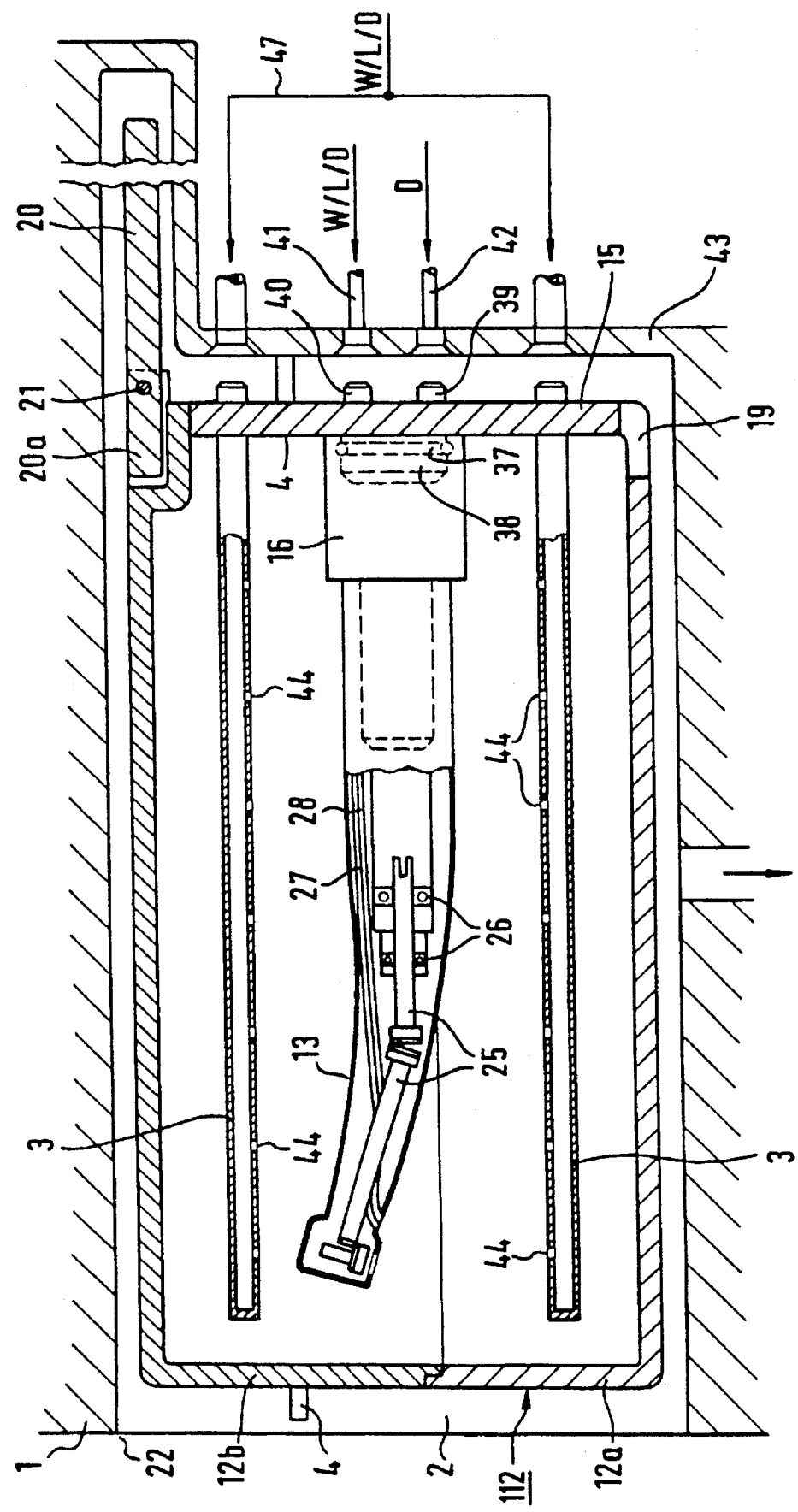
FIG. 9 is a modification of the apparatus and cassette illustrated in FIG. 6.

A modification or embodiment of the cassette is illustrated in FIG. 9 by a cassette generally indicated as 112. This modification is with regard to the nozzle arms 3. For example, the nozzle arms can be component parts of the cassette, as shown in the exemplary embodiment of FIG. 9, and are mounted in the backwall 15. In addition, even though this would be relatively involved, the nozzle arms can be pivoted around their longitudinal axis and can also be potentially arranged movable in an axial direction. The cover shown in FIGS. 3–5 can alternatively also be a component part of the lower cassette or can be allocated to both cassette halves.

Although various minor modifications may be suggested by those versed in the art, it should be understood that we wish to embody within the scope of the patent granted hereon all such modifications as reasonably and properly come within the scope of our contribution to the art.

We claim:

1. In an apparatus for cleaning medical articles including dental instruments, said apparatus including a cassette accepting the articles, a chamber for receiving the cassette and being closable pressure-tight, said cassette containing adapters for holding the articles with a plurality of nozzles in the cassette being connected to a delivery line and being directed onto each of the articles end being arranged around the article for delivering cleaning fluid for treatment on the exterior surface of each Of the articles via said nozzles, the improvements comprising means for supplying the fluid in a pulsating fashion with pulse, pauses, means for introducing gas under high pressure in a pulsating fashion into the delivery line of the cleaning fluid to the nozzles during pulse pauses of the fluid delivery.

2. In an apparatus according to claim 1, wherein the adapters contain means for holding the article as well as means for introducing liquid and gas agents for treating any moving parts of the article and for cleaning any media channels contained in said article.

3. In an apparatus according to claim 1, wherein the nozzles are part of the apparatus chamber and the cassette is provided with openings for the admission and discharge of treatment agents from the nozzles.

4. In an apparatus according to claim 3, wherein the nozzles are arranged as nozzle arms that extend along the chamber and are secured to a back end of the chamber, said nozzle arms being arranged so that the surface of the article can be completely charged with the treatment agent, the cassette having a backwall provided with said openings through which the nozzle arms extend when the cassette is inserted in the chamber.

5. In an apparatus according to claim 4, wherein the nozzle arms are arranged in two rows with a row of adapters therebetween.

6. In an apparatus according to claim 5, wherein one row of nozzle arms is offset from the other of the two rows of nozzle arms so that each nozzle arm of said one row acts on two adjacent adapters.

7. In an apparatus according to claim 3, wherein the nozzles are situated as nozzle arms and are arranged around each adapter at an angle of 120° relative to one another.

8. In an apparatus according to claim 7, wherein nozzles are arranged offset relative to one another by a small angle with reference to a plane of reference proceeding through a longitudinal axis of the arm.

9. In an apparatus according to claim 8, wherein the offset is aligned with the nozzles proceeding above and below the reference plane in alteration.

10. In an apparatus according to claim 1, wherein the nozzles are arranged as part of the cassette and the cassette is provided with openings for the admission and discharge of treatment agents to the nozzles.

11. In an apparatus according to claim 1, wherein the adapters are held on a backwall of a cassette in an easily exchangeable fashion.

12. In an apparatus according to claim 11, wherein at least one adapter is provided for holding a dental instrument which comprises line channels for the delivery of treatment agents to the interior of the instrument.

13. In an apparatus according to claim 12, wherein each adapter contains a control valve which closes all delivery lines of an adapter not occupied with an instrument.

14. In an apparatus according to claim 12, wherein a plurality of adapters are provided for different instruments and each adapter has means with identical connecting dimensions for mounting the adapter on the housing wall of the cassette.

15. In an apparatus according to claim 1, wherein the cassette is composed of two housing halves formed by a transverse division and connectible to one another, one housing half having a base member carrying an adapter and the other haft being a cover member having guide elements for guidance of the cassette in the chamber of the apparatus.

16. In an apparatus according to claim 1, wherein the nozzles are arranged as part of the chamber and the cassette is provided with openings through which the nozzles extend, said cassette including cover means for closing said openings when the cassette is removed from said chamber, said cover means having control means for lifting the cover to expose said openings when the cassette is inserted in the chamber.

17. In an apparatus according to claim 16, wherein the cover means is a plate pivotably held on a backwall of the cassette, said control means being said plate having a projection that engages a housing edge upon introduction of the cassette into the chamber to cause the plate to move to a position uncovering said openings.

18. In an apparatus according to claim 1, wherein the cassette is composed of a sterilizable plastic.

19. In an apparatus according to claim 1, wherein control means are present for controlling the delivery of the gas and of the cleaning fluid to create the pulse pauses of the delivery of the cleaning fluid.

20. In an apparatus according to claim 19, wherein the control means is designed so that the pulse frequency for the surge-like delivery of gas amounts to approximately 3 Hz.

* * * * *